United States Patent [19]

Horn et al.

[11] Patent Number: 5,358,845
[45] Date of Patent: Oct. 25, 1994

[54] METHOD OF DETECTING PROTEINS IN BODY FLUIDS AND MEANS OF CARRYING OUT THE METHOD

[75] Inventors: Jurgen Horn, Egelsbach; Heike Nebel-Schickel, Hammersbach-Markobel, both of Fed. Rep. of Germany

[73] Assignee: Biotest AG, Dreieich, Fed. Rep. of Germany

[21] Appl. No.: 997,618

[22] Filed: Dec. 24, 1992

Related U.S. Application Data

[63] Continuation of Ser. No. 786,491, Nov. 1, 1991, abandoned.

[30] Foreign Application Priority Data

Nov. 6, 1990 [DE] Fed. Rep. of Germany ....... 4035174

[51] Int. Cl.$^5$ ................ G01N 33/569; G01N 33/543; C12Q 1/00
[52] U.S. Cl. ......................... 435/5; 435/7.1; 435/7.92; 435/7.94; 435/962; 436/501; 436/518; 436/18; 436/826
[58] Field of Search ............. 435/5, 7.1, 7.92, 7.94, 435/962; 436/501, 518, 16, 18, 826

[56] References Cited

U.S. PATENT DOCUMENTS

| 4,164,558 | 8/1979 | Schulthess et al. | 435/962 |
|---|---|---|---|
| 4,362,697 | 12/1982 | Tubb et al. | 436/826 |
| 4,444,880 | 4/1984 | Tom | 435/961 |
| 4,591,552 | 5/1985 | Neurath | 435/5 |
| 4,618,486 | 10/1986 | Lundblad | 435/962 |
| 4,692,330 | 9/1987 | Ryohei | 435/962 |
| 4,810,630 | 3/1989 | Craig | 435/962 |
| 4,834,298 | 6/1989 | Kays | 436/175 |
| 4,931,385 | 6/1990 | Block et al. | 436/826 |
| 4,981,786 | 1/1991 | Dafforn et al. | 435/805 |
| 5,006,464 | 4/1991 | Chu | 435/5 |

FOREIGN PATENT DOCUMENTS

| 0133272 | 7/1984 | European Pat. Off. . |
|---|---|---|
| 0202093 | 5/1986 | European Pat. Off. . |
| 0303062 | 7/1988 | European Pat. Off. . |
| 0303980 | 8/1988 | European Pat. Off. . |
| 0445650 | 8/1988 | European Pat. Off. . |
| 253683 | 1/1988 | Fed. Rep. of Germany ...... 435/962 |
| 9010232 | 7/1990 | PCT Int'l Appl. . |

OTHER PUBLICATIONS

Crofts et al. "Evaluatino of enzyme-linked immunosorbent assays. a method of data analysis"? J. Vir. Meth. 22 pp. 51–59, 1988.

Primary Examiner—Christine M. Nucker
Assistant Examiner—Chris Dubrule
Attorney, Agent, or Firm—Sprung Horn Kramer & Woods

[57] ABSTRACT

The invention concerns a method of detecting proteins, especially HIV and CMV antibodies in body fluids using solid-phase immune reaction with a buffer containing an animal serum and/or a non-ionic surfactant in a phosphate or carbonate buffer together with further additives selected from inorganic salts, water-soluble polymers, organic compounds, and propionic acid and their derivatives and mixtures. The buffer makes it possible to reliably eliminate false positive results.

9 Claims, No Drawings

METHOD OF DETECTING PROTEINS IN BODY FLUIDS AND MEANS OF CARRYING OUT THE METHOD

This application is a continuation of application Ser. No. 786,491, filed Nov. 1, 1991 now abandoned.

The present invention concerns, first, a method of detecting proteins in body fluids by solid-phase immune reaction and, second, means for carrying it out, whereby results are improved by eliminating false-positive reactions. The method in accordance with the invention is particularly appropriate for detecting antibodies against human immunodeficiency virus (HIV) or against cytomegaly virus (CMV) in serum or plasma.

The process of detecting such proteins as antigens, antibodies, and haptens in body fluids is extremely delicate. The detection is carried out in the solid phase by what is called sandwiching or a modification thereof. A reaction partner is bonded to the solid phase, which comprises polystyrene spheres or polystyrene latex, or to the surface of microtest plates.

On the other hand the solid phase can also consist of other polymers known to one of skill in the art and simply coated with the reaction partner, the antigen for example. It is then reacted with the proteins that are to be detected in the fluid, which are conventionally revealed, by enzyme labeling (cf. German OS 3 930 376.4, corresponding to U. S. Ser. No. 580,416, filed Sep. 10, 1990, now pending), radioactive labeling, or rare-earth chelate complexing for example.

European A 0 292 809 discloses a method of detecting proteins wherein one partner reacts in an aqueous solution with another partner covalently bonded to a solid phase. The buffer contains a non-ionic surfactant of the formula

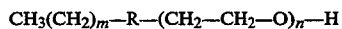

$$CH_3(CH_2)_m-R-(CH_2-CH_2-O)_n-H$$

wherein
R=O, NH, CH=CH—$(CH_2)_p$—O,
m=3–26,
n=7–40, and
p=5–15.

A buffer of this type is claimed to prevent overall fluctuating, excessive, or insufficient results in immunological tests. Nothing is said, however, about suppressing the false-positive results that often occur in detecting specific proteins, viruses for example.

Nevertheless, such results have been observed especially with respect to detecting antibodies to HIV or CMV without any positive results actually being present. Pooled sera or plasmas in particular can react unspecifically positive in testing for HIV or CMV antibodies.

U.S. Pat. No. 5,839,298 discloses a method of inactivating HIV antibodies with an accordingly higher immunoassay specificity. The inactivating buffer is a salt-phosphate buffer in conjunction with 0.05 to 1% salt, preferably a chloride, and a non-ionic surfactant (0.05–0.5%) and accordingly exhibits a specific conductivity (21– 35 mS/cm).

Although such a system can be employed to inactivate HIV, nothing is said about how HIV antibodies can be reproducibly and definitively detected and false results reliably eliminated.

The object of the present invention is accordingly a method of detecting proteins in body fluids, especially antibodies to HIV or CMV in sera or plasmas, that will lead to reliable results and eliminate unspecific, positive reactions.

This object is attained in accordance with the invention in that a diluting buffer that contains a phosphate buffer solution or carbonate buffer, 5 to 75% by volume of animal sera, and/or 0.01 to 5% by weight or volume of a non-ionic surfactant, and other substances selected from inorganic salts, water-soluble polymers, organic compounds, and propionic acid, and their derivatives and mixtures is added to the sample containing the protein to be detected.

The diluting buffer of serum and/or surfactant will also preferably be 0.02 to 0.08M inorganic salts and/or propionic acid or its water-soluble salts, sodium propionate for example.

Especially appropriate are formulations that contain, in addition to serum, calf's serum for example, and/or surfactant and the aforesaid salts, 0.01 to 2.5% by weight (0.2–0.4M) of such water-soluble polymers as polyvinyl pyrrolidone, polyvinyl sulfate, polyacrylamide, dextran, polyethylene glycol, methoxypolyethylene glycol, and polyvinyl alcohol.

It has also been demonstrated of advantage for the buffer of serum and surfactant in accordance with the invention to be 0.02 to 0.25M of organic compounds selected from urea, guanidium salts, glycerol, or glycine, and such chaotropic ions as thiocyanates in the capacity of additive.

The animal sera employed in accordance with the invention include in particular calf's and goat's serum inactivated (for example for 1 hour at 55° C.) and filtered sterile prior to use. Mixtures of such sera, one containing 25% calf's serum and 25% goat's serum for example, are also appropriate for the formulations in accordance with the invention.

Appropriate non-ionic surfactants include esterified polyoxyethylenes of the formula

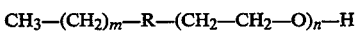

$$CH_3-(CH_2)_m-R-(CH_2-CH_2-O)_n-H$$

wherein
R=O, NH, CH=CH—$(CH_2)_p$—O,
m=6–8,
n>40, and
p=6–8
(polymerization degree>40) and etherified polyoxyethylenes.

Especially preferred are Tween 20, Tergitol, Triton, and Lubrol. They are added at 0.01 to 5% by weight for solids or by volume of liquids.

The inorganic salts in particular include such alkaline halides as sodium fluoride, bromide and iodide, perchlorates, iodates and bromates, and sodium azide, sodium fluoride being especially preferred.

Especially appropriate as a water-soluble polymer is polyvinyl pyrrolidone.

The so characterized diluting buffer makes it possible reliably and reproducibly to detect proteins in body fluids.

The following formulations have been demonstrated particularly appropriate and are accordingly preferred:

A diluting buffer containing a phosphate-buffered sodium-chloride solution with 0.05% by volume Tween 20 and inorganic salts (0.02–0.8M), especially sodium fluoride or sodium iodide (preferably 0.1–0.5M) and/or propionic acid and its derivatives (0.1–0.5M).

A diluting buffer containing a phosphate-buffered sodium-chloride solution with 5 to 25%, especially 5 to 20%, and highly preferably 10% by volume of calf's serum along with sodium fluoride or iodide (0.02–0.8M and especially 0.1–0.5M) and/or propionic acid (0.02–0.8M) and their derivatives and optionally water-soluble polymers of the aforesaid type, especially 0.01 to 2.5% by weight of polyvinyl pyrrolidone.

Another particularly appropriate group of diluting buffers that can be employed in accordance with the invention includes those containing a carbonate buffer (e.g. 0.05M) with calf's serum, especially 5 to 25% by volume, and/or Tween 20 (0.1–0.5% by volume) along with inorganic salt as hereintofore described, especially sodium fluoride or iodide (0.02–0.8M). Also particularly appropriate are formulations of the aforesaid type that, in addition to or instead of the sodium fluoride, contain propionic acid or its derivatives, especially its sodium salts (0.02–0.8M, especially 0.12–0.16M).

Formulations containing a carbonate buffer, calf's serum (especially 5 to 25% by volume), inorganic salts as hereinabove described and/or propionic acid, and water-soluble polymers, especially polyvinyl pyrrolidone 90 (MW=90 000, 0.01–2.5% by weight).

The sample to be tested is treated with these buffers, and the proteins detected by the solid-phase method described in German OS 3 930 376.4. A reaction partner is bonded to the solid phase (polystyrene, microtest plate, and other polymers) and converted with the reaction partner in the sample. The actual detection is carried out with a labeled third partner that bonds to the second.

The labeling can be carried out with an enzyme (peroxidase or alkaline phosphatase), radioactively ($^{125}$I), or with rare-earth chelates (europium chelate) followed by detecting fluorescence.

The invention will now be described with reference to the following examples:

EXAMPLE 1

The seven European sera in the following list were examined for HIV antibodies by the sandwich technique. Documentation was enzymatically determined by observing the extinction of the reaction product with a spectrophotometer (492 nm, reference wavelength 570–650 nm). See also the Paul Erlich Institute test procedures Biotest Anti-HIV-1/-2 (105a/90) and Biotest Anti-CMV IgG ELISA (62a/86).

The molarities are those of the substances in the finished diluting buffer.

List of Sera
Serum 1. Negative European serum
Serum 2. Positive European serum
Serum 3. Serum 2 diluted 1:100
Serum 4. Serum 2 diluted 1:200
Serum 5. Negative European serum
Serum 6. Negative European-serum pool
Serum 7. Negative European-serum pool
List of Diluting Buffers Reference:

A.
Phosphate-buffered sodium-chloride solution with 0.05% Tween 20 by volume (reference).

In Accordance with the Invention

B.
A+0.1 molar sodium fluoride

C.
A+0.5 molar sodium fluoride

D.
A+0.1 molar propionic acid

E.
A+0.1 molar sodium propionate +0.1 molar sodium fluoride

F.
A+10% by volume calf's serum +0.5% NP 40

G.
A+25% by volume calf's serum

H.
A+0.1 molar sodium iodide

I.
A+0.1 molar sodium bromide

J.
A+0.05 molar guanidinium sulfate

K.
A+0.5 molar sodium perchlorate

L.
A+0.1 molar sodium thiocyomate

M.
A+0.5% by weight of POES 100 (polyoxyethylene stearate 100 (with the degree of polymerization of the oxyethylene being 100).

N.
A+10% by volume calf's serum +0.5% by volume NP 40 (Noridet P 40 octylphenolethylene-oxide condensate), +0.05 molar sodium iodide, +0.1 molar propionic-acid sodium salt.

The results of these studies are summarized in the following Table 1:

TABLE 1

| Buffer | Serum 1 | 2 | 3 | 4 | 5 | 6 | 7 |
|---|---|---|---|---|---|---|---|
| Reference standard: | | | | | | | |
| A. | 0.022 | >3.0 | 1.167 | 0.546 | 0.410 | 0.171 | 0.368 |
| In accordance with the invention | | | | | | | |
| B. | 0.001 | >3.0 | 0.748 | 0.397 | 0.019 | 0.007 | 0.054 |
| C. | 0.002 | >3.0 | 0.488 | 0.316 | 0.018 | 0.004 | 0.018 |
| D. | −0.001* | >3.0 | 0.568 | 0.334 | 0.020 | 0.003 | 0.028 |
| E. | −0.004* | >3.0 | 0.827 | 0.435 | 0.012 | 0.002 | 0.016 |
| F. | −0.002* | >3.0 | 1.063 | 0.528 | 0.004 | 0.003 | 0.002 |
| G. | 0.000 | >3.0 | 1.188 | 0.644 | 0.020 | 0.006 | 0.035 |
| H. | 0.001 | >3.0 | 0.815 | 0.446 | 0.025 | 0.015 | 0.014 |
| I. | 0.002 | >3.0 | 0.832 | 0.458 | 0.022 | 0.012 | 0.016 |
| J. | −0.001* | >3.0 | 0.722 | 0.356 | 0.058 | 0.032 | 0.038 |
| K. | −0.002* | >3.0 | 0.685 | 0.317 | 0.029 | 0.021 | 0.032 |
| L. | −0.003* | >3.0 | 0.652 | 0.328 | 0.010 | 0.008 | 0.014 |
| M. | −0.001* | >3.0 | 0.798 | 0.389 | 0.016 | 0.029 | 0.012 |
| N. | 0.000 | >3.0 | 1.059 | 0.628 | 0.012 | 0.002 | 0.004 |
| O. | −0.001* | >3.0 | 1.156 | 0.657 | 0.010 | 0.001 | 0.002 |

*Negative extinctions may occur in negative samples when the reagent base-line values are subtracted.

Extinctions of less than 0.3 represent reliable (applicable) negative results, and levels of more than 0.3 represent definitive positive results.

As will be evident from these results, the samples with the conventional diluting buffer consisting of a phosphate-buffered sodium-chloride solution and Tween 20 were not correctly identified. Samples 5 and 7 exhibit positive results even though they are HIV-negative sera.

The tests carried out with the method in accordance with the invention all provided correct results, no false positives, that is, even when the sample had been diluted to 1:100 or even 1:200.

EXAMPLE 2

Negative African sera 8–12 were tested as described with reference to Example 1 by determining the extinctions for the presence of HIV antibodies.

Table 2 summarizes the results.

TABLE 2

| Buffer | Serum 8 | 9 | 10 | 11 | 12 |
|---|---|---|---|---|---|
| Reference standard: | | | | | |
| A. | 1.486 | 0.488 | 0.712 | 0.255 | 0.981 |
| In accordance with the invention: | | | | | |
| Q.** | 0.227 | 0.084 | 0.092 | 0.018 | 0.112 |
| R.*** | 0.138 | 0.068 | 0.076 | 0.016 | 0.098 |
| B. | —* | 0.097 | 0.098 | 0.155 | 0.199 |
| G. | —* | 0.132 | 0.216 | 0.036 | 0.136 |

*Not tested
**A + 25% calf's serum, + 0.5% NP 40 + 0.05M sodium iodide + 0.1M sodium propionate
***A + 25% calf's serum + 0.15M sodium fluoride + 0.1M sodium propionate + 0.1% polyvinyl sulfate As these results indicate, the method in accordance with the invention can also be reliably employed to test African sera, although, as comparison with the conventional standard buffer A suggests, false positives are often obtained with African sera in particular.

EXAMPLE 3

As described with reference to Examples 1 and 2, European serum 7 and the sera in the following list were tested for specificity to CMV antibodies.

Serum 13. Positive
Serum 14. Positive diluted 1:100 in negative
Serum 15. Negative
Serum 16. Negative The results are summarized in Table 3.

TABLE 3

| Buffer | Serum 7 | 13 pos. | 14 pos. | 15 neg. | 16 neg. |
|---|---|---|---|---|---|
| Reference Standard | | | | | |
| A. | 0.168 | 2.417 | 0.228 | 0.256 | 0.306 |
| In accordance with the invention | | | | | |
| Q. | 0.014 | 2.428 | — | 0.049 | 0.026 |
| R. | 0.012 | 2.432 | — | 0.064 | 0.018 |
| S.* | 0.017 | 2.678 | 0.449 | 0.051 | 0.207 |
| T.** | 0.020 | 2.665 | 0.476 | 0.057 | 0.031 |

*A + 40% by volume calf's serum + 0.4% by weight PVP 90 (polyvinyl pyrrolidone with a MW of 90 000) + 0.1% by weight sodium azide
**A + 20% by volume calf's serum + 20% by volume goat serum + 0.4% by weight PVP 90 = 0.1% by weight sodium azide + 0.1 molar sodium propionate.

EXAMPLE 4

The following formulations were employed as in Example 1 to test for the presence of HIV antibodies. The negative African sera 8 to 12 and the serum 4 (positive European serum diluted 1:200) were employed.

The results are summarized in the following Table 4:

TABLE 4

| Buffer | 8 | 9 | 10 | 11 | 12 | 4 |
|---|---|---|---|---|---|---|
| U. | 0.121 | 0.072 | 0.098 | 0.002 | 0.117 | 0.669 |
| V. | 0.118 | 0.085 | 0.077 | 0.032 | 0.098 | 0.651 |
| W. | 0.105 | 0.065 | 0.052 | 0.028 | 0.089 | 0.712 | where
U is A
25% by volume calf's serum
0.15 molar sodium fluoride

TABLE 4-continued

| Buffer | 8 | 9 | 10 | 11 | 12 | 4 |
|---|---|---|---|---|---|---|

0.1 molar propionic acid sodium salt
V is 0.01 molar sodium chloride solution buffered to a pH of 7.2 with TRIS (trishydroxymethyl-amino methane)
0.075% by weight POES 100 (polyoxyethylene stearate)
25% by volume calf's serum
5% by volume goat serum
0.15 molar sodium fluoride
0.1 molar propionic acid sodium salt
W is 0.05 molar TRIS
60% by volume calf's serum
0.15 molar sodium fluoride
0.15 molar propionic acid sodium salt As will be evident from these results, the buffers in accordance with the invention, especially those that contain serum and/or surfactant, sodium fluoride and sodium propionate, can be utilized reliably to demonstrate either the presence or absence of HIV antibodies.

EXAMPLE 5

The African sera 8 to 12 from Example 2 and the positive European serum 14 diluted 1:100 in negative serum were then tested for HIV antibodies as described in Example 3.

The results are summarized in the following Table 5.

TABLE 5

| Diluting buffers | Extinction for probe 8 | 9 | 10 | 11 | 12 | 13 |
|---|---|---|---|---|---|---|
| Reference standard: | | | | | | |
| 0.05M carbonate buffer | 1.655 | 0.617 | 0.938 | 0.327 | 1.103 | 0.652 |
| In accordance with the invention: | | | | | | |
| 0.05M carbonate buffer 25% by vol. calf's serum 0.15M NaF | 0.135 | 0.056 | 0.092 | 0.018 | 0.114 | 0.662 |
| 0.05M carbonate buffer 25% by vol. calf's serum 0.15 molar NaF 0.15 molar sodium propionate 0.4% by weight PVP 90 | 0.082 | 0.027 | 0.035 | 0.012 | 0.036 | 0.759 |
| 0.05M carbonate buffer 0.15 molar NaF 0.12 molar sodium propionate | 0.255 | 0.151 | 0.166 | 0.089 | 0.209 | 0.631 |
| 0.05M carbonate buffer 25% by vol. calf's serum 0.15 molar solar propionate 0.4% by weight PVP 90 | 0.162 | 0.042 | 0.065 | 0.028 | 0.086 | 0.776 |

It will be appreciated that the instant specification and claims are set forth by way of illustration and not limitation, and that various modifications and changes may be made without departing from the spirit and scope of the present invention.

We claim:

1. A diluting buffer solution for detecting proteins in body fluids by immunoassay, comprising a phosphate or carbonate buffer solution containing about
   25% calf serum
   0.1 to 0.15M NaF and
   0.1 to 0.15M Na propionate.

2. A buffer solution according to claim 1, containing about
   0.15M NaF
   0.1M Na propionate and 0.05 Tween 20 volume %.

3. A buffer solution according to claim 1, containing a carbonate buffer.

4. A buffer solution according to claim 1, wherein the solution is 0.05M carbonate.

5. In a method for sandwich immunoassay of a second reaction partner protein in a body fluid, said method comprising the following steps:

(a) bonding a first reaction partner to a solid phase;

(b) reacting the first reaction partner with a buffer solution containing the second reaction partner to yield a conjugate of the first reaction partner and the second reaction partner;

(c) reacting said conjugate with a third reaction partner to yield a second conjugate of the first reaction partner, the second reaction partner and the third reaction partner, said third reaction partner containing an enzymatic, radioactive or fluorescent label and said third reaction partner reacting with the second reaction partner; and (d) detecting the second reaction partner by detecting the enzymatic, radioactive or fluorescent label, wherein the improvement comprises employing as the buffer solution a phosphate or carbonate buffer solution according to claim 1, whereby there is a reduction in false positives.

6. The method according to claim 5, wherein the buffer solution contains about 0.1M Na propionate and 0.05 Tween 20 volume %.

7. The method according to claim 5, wherein the buffer solution contains a carbonate buffer.

8. The method according to claim 5, wherein the buffer solution is 0.05M carbonate.

9. The method according to claim 5, wherein the second reaction partner comprises an antibody to HIV or CMV.

* * * * *